United States Patent
Moshier et al.

(10) Patent No.: US 7,572,360 B2
(45) Date of Patent: Aug. 11, 2009

(54) ELECTROCHEMICAL FATIGUE SENSOR SYSTEMS AND METHODS

(75) Inventors: Monty Moshier, Washington, UT (US);
William I. Berks, Manhattan Beach, CA (US)

(73) Assignee: Fatigue Solutions Corp., Los Angeles, CA (US)

( * ) Notice: Subject to any disclaimer, the term of this patent is extended or adjusted under 35 U.S.C. 154(b) by 706 days.

(21) Appl. No.: 11/240,677

(22) Filed: Sep. 30, 2005

(65) Prior Publication Data

US 2007/0074976 A1    Apr. 5, 2007

(51) Int. Cl.
*G01N 17/04* (2006.01)
*G01N 27/26* (2006.01)

(52) U.S. Cl. .................................. 205/775.5; 204/404
(58) Field of Classification Search ......... 204/400–430; 205/775.5, 776, 776.5, 777
See application file for complete search history.

(56) References Cited

U.S. PATENT DOCUMENTS

| | | | |
|---|---|---|---|
| 5,505,827 A | | 4/1996 | Yamashita et al. |
| 5,771,890 A | * | 6/1998 | Tamada .................... 600/347 |
| 6,026,691 A | | 2/2000 | Laird et al. |
| 6,267,017 B1 | * | 7/2001 | Miller et al. .................. 73/866 |
| 6,328,878 B1 | | 12/2001 | Davis et al. |

* cited by examiner

*Primary Examiner*—Alex Noguerola
(74) *Attorney, Agent, or Firm*—Kenyon & Kenyon LLP

(57) ABSTRACT

A method for determining a fatigue status of a growing crack in a substrate. An electrochemical sensor device is provided and includes an electrode formed from a stainless steel mesh. The electrochemical device has a bottom surface that contacts the substrate. The bottom surface is coated with an adhesive layer, and a release paper is attached to the adhesive layer. The release paper is separated from the adhesive layer, thereby exposing the adhesive layer. The electrochemical sensor device is secured to the substrate by bringing the adhesive layer in contact with the substrate and thereby forming an electrolyte cavity bounded in part by the substrate. The adhesive seals the bottom surface of the device to the substrate in order to prevent leakage of electrolyte from the cavity. The cavity is filled with the electrolyte. When the substrate is subjected to cyclic loading, the fatigue status of the growing crack in the substrate is determined in accordance with a measured current between the reference electrode and the substrate.

9 Claims, 4 Drawing Sheets

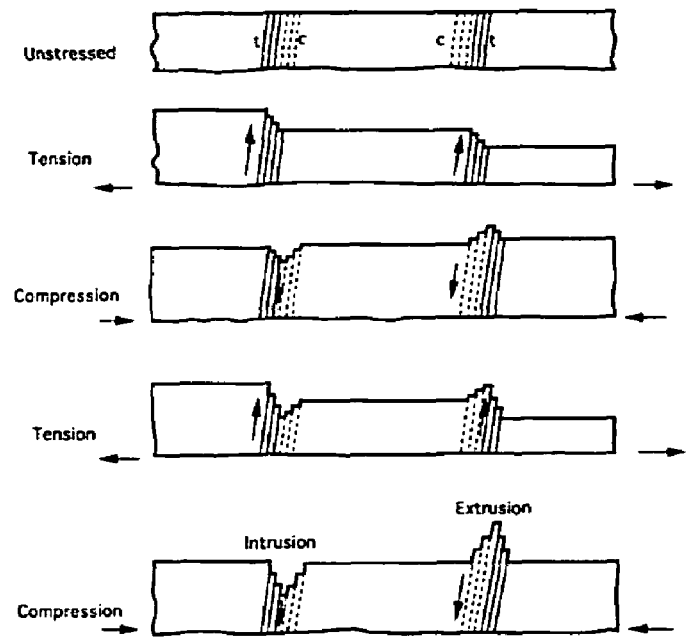
Figure 3 Schematic showing the early stages of crack initiation.
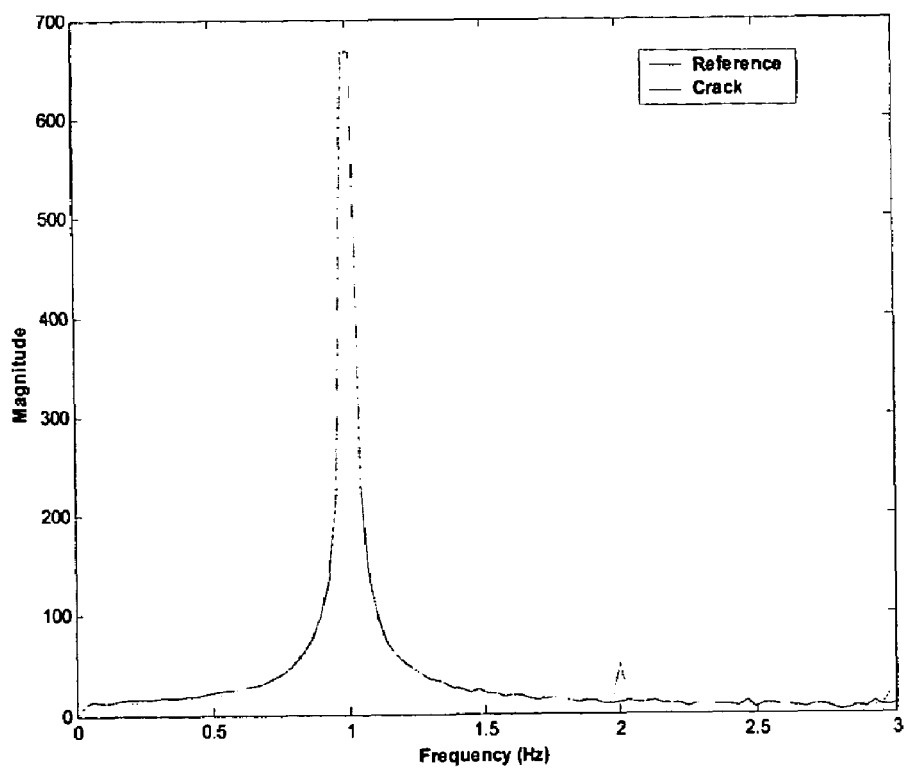
Figure 4. FFT of EFS data when a 0.01 inch crack is growing.

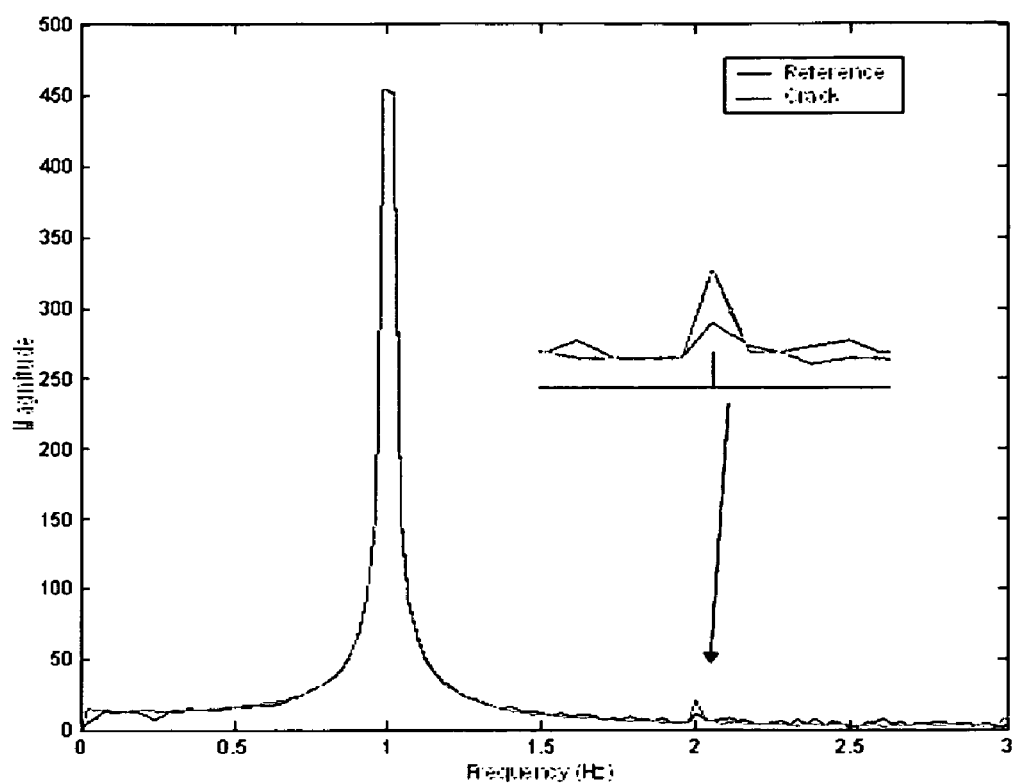
Figure 5 Differential EFS signal comparisons.

ELECTROCHEMICAL FATIGUE SENSOR SYSTEMS AND METHODS

FIELD OF THE INVENTION

The present invention relates generally to electrochemical fatigue sensor devices, and systems and methods for using such devices.

BACKGROUND OF THE INVENTION

Referring now to FIG. 1, there is shown a schematic diagram of an electrochemical fatigue sensor (EFS) device 10, in accordance with the prior art. EFS device 10 can be used to implement a non destructive fatigue crack inspection method for determining if inspected fatigue cracks are actively growing. For example, EFS device 10 may be applied to a fatigue critical location on a laboratory specimen or structure to be inspected. EFS device 10 consists of an electrolyte 12, sensor 14, and a potentiostat (not shown) for applying a constant polarizing voltage between the structure (substrate 16) and the sensor 14.

EFS device 10 works on electrochemical principles. The structure is anodically polarized to create a protective, passive film on the surface to be tested. A polarizing voltage between the structure and the electrode produces a DC base current in the cell. If the structure being interrogated by the EFS undergoes a cyclic stress, then the current flowing in the cell fluctuates in a complex relation to the variation of the mechanical stress state. Thus, an AC current is superimposed on the DC base current. Depending on the material of the structure and the loading conditions as well as the state of the fatigue damage in the structure, the transient current of the cell provides information on the status of the fatigue damage.

The electrochemical conditions imposed during EFS interrogation of a structure are designed to induce a stable passive oxide film on the surface of the material. During cyclic loading, the fatigue process causes micro plasticity and strain localization on a very fine scale. The interaction of the cyclic slip and the passivating process causes temporary and repeated alterations of the passive films. These alterations, including dissolution and repassivating processes, give rise to transient currents.

The EFS transient currents are complex, involving cyclic changes in the electrical double layer at the interface of the metal and the EFS electrolyte, generally possessing the same frequency as that of the mechanical stress, but having a complex phase relationship depending on the specific metal interrogated. In addition, the disruption of the oxide films on the metallic surface by the cyclic slip causes an additional component of the transient current which has double the frequency of the elastic current because plasticity effects occur during both the tensile and compressive parts of the cycle. As fatigue damage develops with accumulated cycles and cracks form, the cracks induce localized plasticity at different parts of the fatigue cycle from those in which the background micro plasticity occurs and in which cracks have not yet formed. The crack-induced plasticity thus introduces higher harmonic components into the transient EFS current. Analysis and calibration of these various current components allow the fatigue crack growth to be determined.

Existing EFS devices, such as that shown in FIG. 1, suffer from numerous drawbacks. For example, known EFS devices are cumbersome to attach to a substrate and fill with electrolyte. Known EFS devices also suffer from poor sensitivity, and the signal processing techniques for analyzing EFS signals generated by such devices also appear to be inadequate. The present invention addresses such shortcomings in the prior art.

SUMMARY OF THE INVENTION

The present invention is directed to a method for determining a fatigue status of a growing crack in a substrate. An electrochemical sensor device is provided and includes an electrode formed from a stainless steel mesh. The electrochemical device has a bottom surface that contacts the substrate. The bottom surface is coated with an adhesive layer, and a release paper is attached to the adhesive layer. The release paper is separated from the adhesive layer, thereby exposing the adhesive layer. The electrochemical sensor device is secured to the substrate by bringing the adhesive layer in contact with the substrate and thereby forming an electrolyte cavity bounded in part by the substrate. The adhesive seals the bottom surface of the device to the substrate in order to prevent leakage of electrolyte from the cavity. The cavity is filled with the electrolyte. When the substrate is subjected to cyclic loading, the fatigue status of the growing crack in the substrate is determined in accordance with a measured current between the reference electrode and the substrate.

In accordance with a further aspect, the present invention is directed to an electrochemical sensor device for determining a fatigue status of a growing crack in a substrate. The system includes a reference electrode formed from a stainless steel mesh material that is substantially impermeable to an electrolyte. The reference electrode has a bottom side that faces the substrate and a top side that faces away from the substrate. At least one opening is provided in the mesh material, said at least one opening being sufficient in size to permit electrolyte to flow through the reference electrode. A first electrolyte cavity is formed between the substrate and the bottom side of the reference electrode. A second electrolyte cavity is formed between the top side of the reference electrode and a cover of the device. An electrolyte inlet port is formed in a wall of the first electrolyte cavity. A bleeder output port is formed in a wall of the second electrolyte cavity. A sensor measures a current between the reference electrode and the substrate when the substrate is subjected to cyclic loading.

In accordance with a still further aspect, the present invention is directed to a method for determining a fatigue status of a growing crack at a suspected fatigue location on a substrate. A first electrochemical sensor device that includes a first reference electrode is provided. A second electrochemical sensor device that includes a second reference electrode is also provided. The first electrochemical sensor device is positioned over the suspected fatigue location on the substrate, and a first current signal between the first reference electrode and the substrate is measured when the substrate is subjected to cyclic loading. The second electrochemical sensor device is positioned at a location on the substrate where fatigue cracking is not probable, and a second current signal between the second reference electrode and the substrate is measured when the substrate is subjected to cyclic loading. The fatigue status of the growing crack at the suspected fatigue location is assessed by comparing information from the first and second current signals.

BRIEF DESCRIPTION OF THE DRAWINGS

FIG. 3 is a diagram illustrating the early stages of the crack initiation process.

FIG. 4 illustrates a FFT of EFS data for a 0.01 inch growing crack, in accordance with the present invention.

FIG. 5 illustrates a comparison between EFS signals from a reference EFS device and a crack monitoring EFS device, in accordance with the differential EFS techniques of the present invention.

DETAILED DESCRIPTION OF THE PREFERRED EMBODIMENTS

Figure 1:
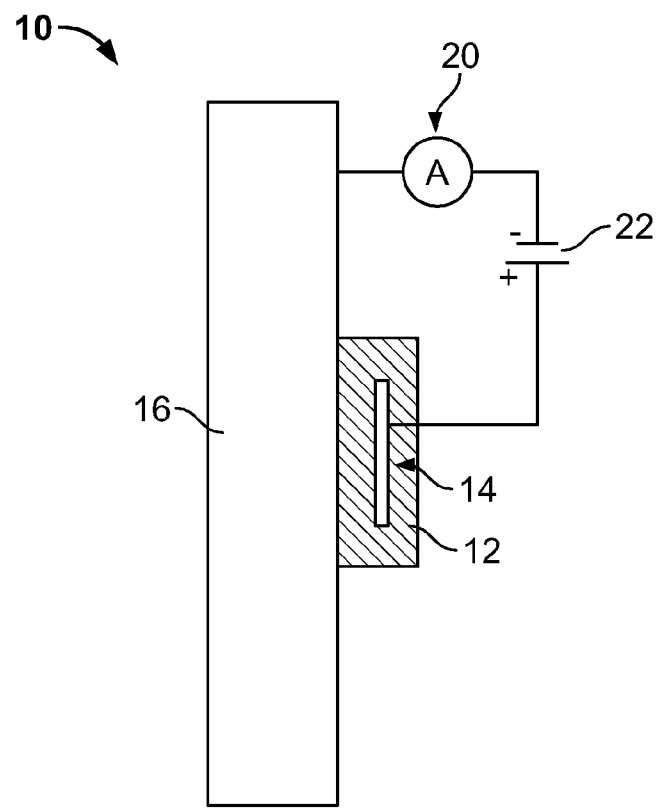
FIG. 1 is a schematic diagram of an electrochemical fatigue sensor device, in accordance with the prior art.
Figure 2A:
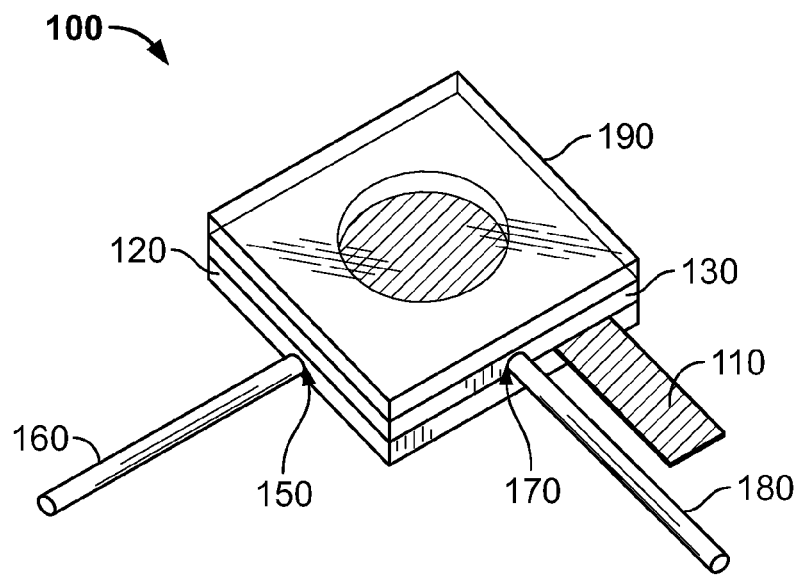
FIG. 2A is an isometric view of an EFS device in accordance with the present invention.
Figure 2B:
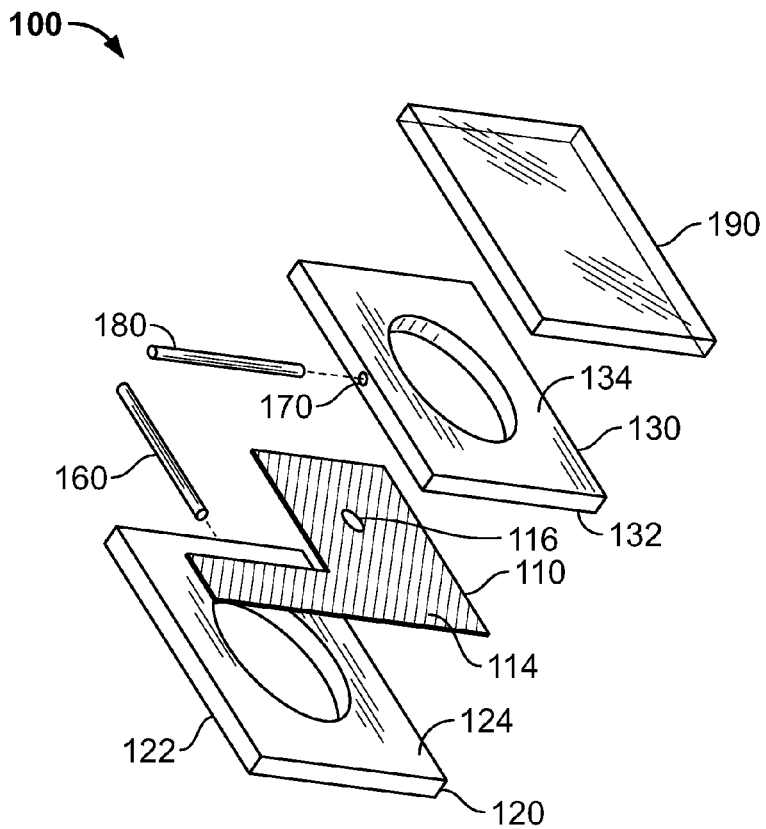
FIG. 2B is an exploded view of the EFS device shown in FIG. 2A.
Figure 2C:
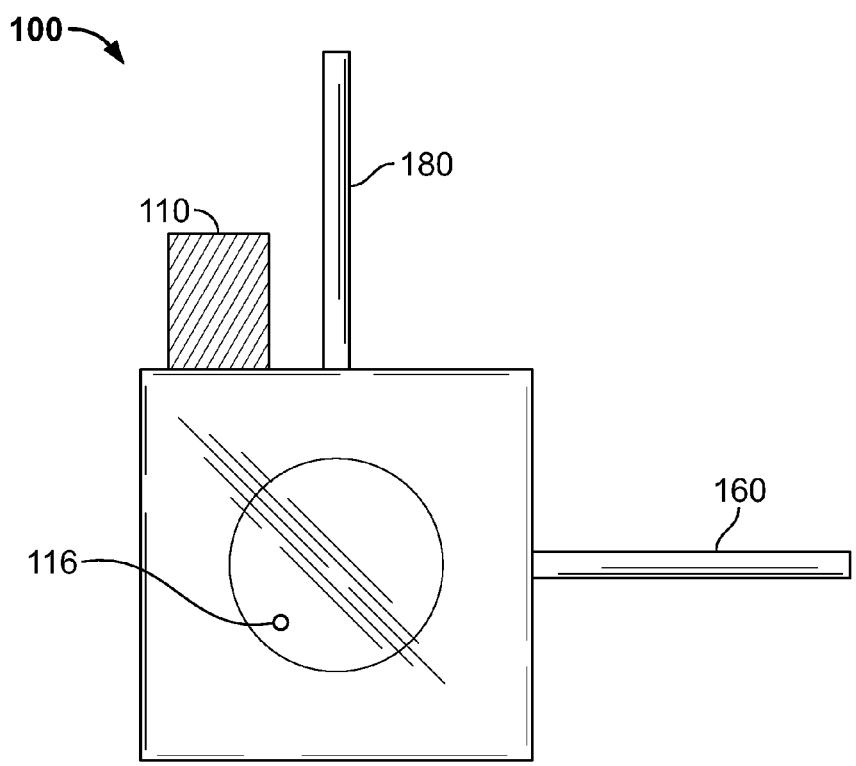
FIG. 2C is a top view of the EFS device shown in FIG. 2B.

Referring now to FIGS. 2A-2C, an EFS device 100 in accordance with the present invention is shown. The sensor includes reference electrode 110 which, in one embodiment, is a mesh made from stainless steel 304. The sensor also includes sections 120, 130 which, in one embodiment, are each made from foam that has been coated on both sides with a pressure sensitive adhesive. In one embodiment, each of sections 120, 130 has a surface area that corresponds to a 2"×2" square, or smaller. A release paper (not shown) is attached to the adhesive on the bottom side 122 of section 120. An electrolyte inlet port 150 is formed in a wall of the section 120. The electrolyte inlet port 150 is coupled to filler tube 160 (e.g., a plastic straw). A bleeder output port 170 is formed in a wall of the section 130. The bleeder output port 170 is coupled to bleeder tube 180 (e.g., a plastic straw). EFS device 100 also include a clear cover plate 190. EFS device 100 is assembled by contacting the adhesive on the top surface 134 of section 130 with the cover plate 190; contacting the adhesive on the bottom surface 132 of section 130 with the top surface 114 of the electrode 110; and contacting the adhesive on the top surface of 124 of section 120 with the bottom surface 112 of electrode 110.

Once assembled, EFS device 100 is ready to be applied to a substrate in order to monitor a fatigue status of a growing crack in the substrate. As mentioned above, the bottom surface 122 of section 120 is coated with an adhesive layer, and a release paper is attached to the adhesive layer. In order to apply EFS device 100 to the substrate, the release paper is separated from the adhesive layer on the bottom surface 122 of section 120, thereby exposing the adhesive layer on the bottom surface 122 of section 120. EFS device 100 is next secured to the substrate by bringing the adhesive layer in contact with the substrate and thereby forming a lower electrolyte cavity bounded on the bottom by the substrate, on the sides by the walls of section 120, and on the top by electrode 110. The adhesive seals the bottom surface 122 of section 120 to the substrate in order to prevent leakage of electrolyte from the lower electrolyte cavity. EFS device 100 also includes an upper electrolyte cavity bounded on the bottom by electrode 110, on the sides by the walls of section 130, and on the top by clear cover 190. In one embodiment, the stainless steel mesh used for forming electrode 110 is substantially impermeable to the electrolyte. At least one opening 116 (shown in FIG. 2C) is provided in the mesh material, the opening 116 being sufficient in size to permit electrolyte to flow through the reference electrode 110.

After EFS device 100 is affixed to the substrate as set forth above, electrolyte is supplied (e.g., pumped) into the device via filler tube 150. The electrolyte initially fills the lower electrolyte cavity. After the lower electrolyte cavity is filled, electrolyte continues to be supplied via filler tube 150, thereby causing electrolyte to flow via opening 116 from the lower electrolyte cavity into the upper electrolyte cavity. The process continues until the upper electrolyte cavity is also filled (e.g., when the electrolyte begins to flow out of bleeder tube 180). Once the fill process is complete, tubes 160, 180 are pinched off and both sides 112, 114 of electrode 110 are covered with electrolyte. During the fill process, the interior of EFS device 100 may be visually monitored through clear cover 190 in order to assure that the device is full of electrolyte and that no bubbles are present. In one embodiment, the electrolyte used for filling the EFS device 100 is:

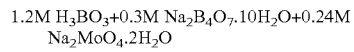

1.2M $H_3BO_3$+0.3M $Na_2B_4O_7.10H_2O$+0.24M $Na_2MoO_4.2H_2O$

It will be understood by those skilled in the art that other electrolyte formulations could also be used.

After EFS device 100 is installed and filled, as described above, a potentiostat (not shown) is coupled to the reference electrode 110 and the substrate, in order to measure current flow between electrode 110 and the substrate. When the substrate is subjected to cyclic loading, the fatigue status of a growing crack in the substrate can be determined in accordance with the measured current between the reference electrode 110 and the substrate (the EFS signal).

The EFS techniques of the present invention offer several advantages over other methods of non-destructive evaluation in that it offers the potential to detect fatigue crack growth as well as having the ability to detect very small cracks (0.005 inches). FIG. 3 illustrates the process of dislocations piling up to form intrusions and extrusions. Such intrusions and extrusions and the formation of a crack at early stages of crack growth may be detected with electro-chemical fatigue sensors in accordance with the present invention.

In the laboratory, it was found that when pure sinusoidal loading is used to fatigue samples, two dominate frequencies are contained in the EFS signal. A fast Fourier transform (FFT) of EFS data for a specimen with a 0.01 inch growing crack revealed both a 1 hz and a 2 hz frequency component, as shown in FIG. 4. The 1 hz component is due to the elastic deformations and the 2 hz component is due to the localized plastic deformations. As the crack grows and the crack growth rate increases the magnitude of the second harmonic at 2 hz increases. Under high loading and prior to fatigue cracking local plasticity caused by the high applied load produces similar secondary harmonics. In order to differentiate between the plasticity caused by cracking and loading, a secondary reference sensor is used. The use of a primary and a secondary sensor together is referred to as differential EFS.

Differential EFS in accordance with the present invention uses two EFS sensors 100, one as the reference (R) and one as the crack measurement (M) sensor, in order to determine a fatigue status of a growing crack at a suspected fatigue location on a substrate. A first EFS device 100 (e.g., the M sensor device) is positioned over the suspected fatigue location on the substrate, and a first current signal between the reference electrode in the C sensor device and the substrate is measured when the substrate is subjected to cyclic loading. A second EFS device 100 (e.g., the R sensor device) is positioned at a location on the substrate where fatigue cracking is not probable, and a second current signal between the reference electrode in the Reference sensor device and the substrate is measured when the substrate is subjected to cyclic loading. The fatigue status of the growing crack at the suspected fatigue location is then assessed by comparing information from the first and second current signals. More specifically, using signal processing the two signals can be compared to determine if a crack is present. Examining FIG. 5 one can see that M measurement sensor provides a larger magnitude than the reference signal thus indicating a crack.

Finally, it will be appreciated by those skilled in the art that changes could be made to the embodiments described above without departing from the broad inventive concept thereof. It is understood, therefore, that this invention is not limited to the particular embodiments disclosed, but is intended to cover modifications within the spirit and scope of the present invention as defined in the appended claims.

What is claimed is:

1. A sensor assembly for an electrochemical fatigue sensor system for determining the fatigue status of a crack in an electroconductive substrate, comprising:
    a body with interior and exterior faces;
    a cavity within the body confining an electrolytic fluid;
    an electrode positioned within the cavity, configured so that the electrolyte is on both sides of the electrode;
    an adhesive that affixes the interior face of the body to the substrate and a second adhesive that affixes a cover plate to the exterior face of the body; and
    a means for adding the electrolyte to the cavity after the sensor assembly is affixed to a substrate.

2. The sensor assembly of claim 1, wherein the body further comprises a plurality of layers that may be assembled on the surface of the substrate.

3. The sensor assembly of claim 1, wherein the electrode is selected from a mesh or sheet of a conductive metal.

4. The sensor assembly of claim 1, wherein the electrode is stainless steel.

5. A method for determining the fatigue status of a crack in a substrate, comprising a set of two sensor assemblies according to claim 4, and the fatigue status of a crack is determined by comparing a measured electric current from the two sensor assemblies.

6. The method of claim 5, wherein each sensor assembly is coupled to a potentiostat that measures current passing through the sensor assembly when a constant voltage is applied to the substrate during cyclic loading of the substrate.

7. The method of claim 5, wherein one sensor assembly is positioned over a suspected fatigue location on the substrate, and the other sensor assembly is positioned where a fatigue crack is unlikely, and the fatigue status of the substrate is assessed by measuring the difference between the electrical signals between the two sensor assemblies.

8. The method of claim 5, wherein data from the potentiostat measurements of current from the sensor assemblies during cyclic loading is transferred to a computer for signal processing to determine the fatigue status of the substrate.

9. A method for determining the fatigue status of a crack in a substrate, comprising a set of two sensor assemblies according to claim 1, wherein
    one sensor assembly is positioned over a suspected fatigue location on the substrate, and the other sensor assembly is positioned where a fatigue crack is unlikely; and
    the fatigue status of a crack is determined by measuring an electric current from each sensor assembly, wherein each measurement is from a potentiostat that measures current passing through the sensor assembly when a constant voltage is applied to the substrate during cyclic loading of the substrate; and
    performing a signal analysis of the potentiostat current measurements to determine the fatigue status of the substrate.

* * * * *

UNITED STATES PATENT AND TRADEMARK OFFICE
CERTIFICATE OF CORRECTION

PATENT NO. : 7,572,360 B2　　　　　　　　　　　　　　　　　　　　Page 1 of 1
APPLICATION NO. : 11/240677
DATED : August 11, 2009
INVENTOR(S) : Moshier et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 894 days.

Signed and Sealed this

Seventh Day of September, 2010

David J. Kappos
*Director of the United States Patent and Trademark Office*